(12) United States Patent
Kirlangic et al.

(10) Patent No.: US 9,872,648 B2
(45) Date of Patent: Jan. 23, 2018

(54) METHOD AND DEVICE FOR COLLECTING DATA FOR POSTUROGRAPHY

(71) Applicant: Forschungszentrum Juelich GmbH, Juelich (DE)

(72) Inventors: Mehmet Eylem Kirlangic, Juelich (DE); Martina Minnerop, Cologne (DE); Christian Spross, Aachen (DE); Boris Boeckem, Juelich (DE); Markus Paulzen, Heinsberg (DE); Manfred Bednarek, Baesweiler (DE); Silke Lux, Huerth (DE); Katrin Amunts, Juelich (DE)

(73) Assignee: Forschungszentrum Juelich GmbH (DE)

( * ) Notice: Subject to any disclaimer, the term of this patent is extended or adjusted under 35 U.S.C. 154(b) by 39 days.

(21) Appl. No.: 14/906,144

(22) PCT Filed: Aug. 5, 2014

(86) PCT No.: PCT/DE2014/000399
§ 371 (c)(1),
(2) Date: Jan. 19, 2016

(87) PCT Pub. No.: WO2015/027973
PCT Pub. Date: Mar. 5, 2015

(65) Prior Publication Data
US 2016/0157770 A1 Jun. 9, 2016

(30) Foreign Application Priority Data

Aug. 27, 2013 (DE) .................. 10 2013 014 092

(51) Int. Cl.
*A61H 7/00* (2006.01)
*A61B 5/00* (2006.01)
*A61B 5/11* (2006.01)

(52) U.S. Cl.
CPC .......... *A61B 5/4561* (2013.01); *A61B 5/1127* (2013.01); *A61B 5/4023* (2013.01);
(Continued)

(58) Field of Classification Search
None
See application file for complete search history.

(56) References Cited

U.S. PATENT DOCUMENTS

| | | | |
|---|---|---|---|
| 3,842,450 A | 10/1974 | Pad | |
| 4,598,717 A * | 7/1986 | Pedotti | A61B 5/1036 600/592 |
| 2007/0055185 A1* | 3/2007 | Trandafir | A61H 1/001 601/90 |

FOREIGN PATENT DOCUMENTS

| | | |
|---|---|---|
| DE | 602 06 125 | 6/2006 |
| DE | 10 2007 014 080 | 9/2007 |

(Continued)

OTHER PUBLICATIONS

"Produkkatalog Haider Bioswing 2005", Apr. 18, 2004 (Apr. 18, 2004), Haider Bloswing, XP002732854, p. 1, 3, 6, 7, pp. 1, 3, 6, 7.
(Continued)

*Primary Examiner* — Erica Lee
(74) *Attorney, Agent, or Firm* — Jordan and Koda, PLLC

(57) ABSTRACT

A method and a device for collecting data for posturography comprising a magnetizable body and an acceleration sensor are located on the platform, which magnetizable body and acceleration sensor are connected to a computer by means of an A/D converter. An electromagnet is located under the platform and is attached so as to be displaceable in two axes parallel to the plane of the platform, wherein the electromagnet is connected to an A/D converter and a power supply by means of a circuit, and a time-variable display, which is connected to the A/D converter, and a digital camera which are connected to the computer. By means of the method and
(Continued)

the device it is now possible to standardize posturographic measurements, simultaneously detect the acceleration and the position of the platform, and more variably carry out provocations.

17 Claims, 1 Drawing Sheet

(52) U.S. Cl.
CPC ............ *A61B 5/742* (2013.01); *A61B 5/1128* (2013.01); *A61B 2562/0219* (2013.01)

(56) References Cited

FOREIGN PATENT DOCUMENTS

| DE | 10 2012 017 219 | | 7/2013 | |
|----|---|---|---|---|
| EP | 1 310 213 | | 5/2003 | |
| EP | 2702975 | A1 * | 3/2014 | ............ A61H 1/005 |

OTHER PUBLICATIONS

Anonymous: "LED Video SUNC Cable, 3 M—OUT103" Biopac Systems, Inc. p. 1, Sep. 2, 2011 (Sep. 2, 2011), XP002732855, Retrieved from the Internet: URL:http://www.biopac.com/led-cable-flash-video-sync [retrieved on Nov. 21, 2014] the whole document.

Anonymous: "Haider BioSwing Motion-Feedback-System fuer Posturomed", Idealo, p. 1, Sep. 1, 2012 (Sep. 1, 2010), XP002732858, Retrieved from the Internet: URL:http://www.idealo.de/preisvergleich/OffersOfProduct/2434415_-motion-feedback-system-fuer-posturomed-haider-bioswing.html [retrieved on Nov. 21, 2014] the whole document.

Visser J E et al: "Dynamic posturography in Parkinson's disease: diagnostic utility of the @?first trial effect@?", Neuroscience, New York, NY, US, Bd. 168, Nr. 2, Jun. 30, 2010 (Jun. 30, 2010), Seiten 387-394, XP027052903, ISSN: 0306-4522 [gefunden am Apr. 7, 2010].

* cited by examiner

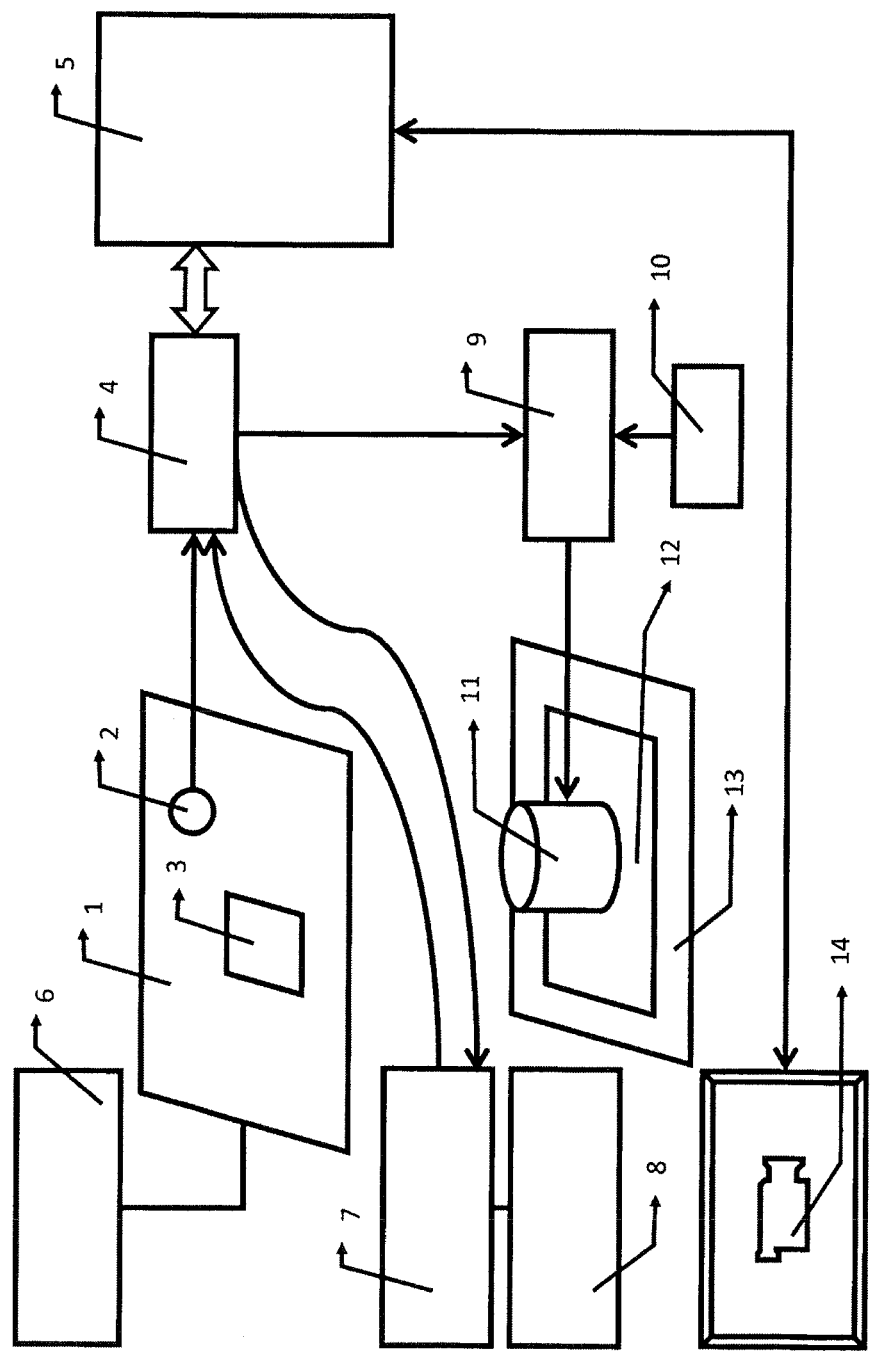

METHOD AND DEVICE FOR COLLECTING DATA FOR POSTUROGRAPHY

The invention relates to a method and a device for collecting data for posturography.

BACKGROUND OF THE INVENTION

Devices for posturography are used for determining the functional ability of balance regulation in the standing position, wherein, for example, the lower extremities are loaded by the action of a force. The devices according to the prior art comprise, for example, a swingable platform, on which healthy persons, serving as test subjects, patients, or animals, can stand. Such a swingable platform is connected at the corners thereof to springs. Optionally, such a device can be equipped with a mechanical provocation unit, which can be installed in one of the two horizontal axes of the platform. Such devices are known from the company Haider-Bioswing GmbH.

The devices according to the prior art have disadvantages, however.

The device according to the prior art does not permit intra- and inter-individual comparability of measurements within the scope of studies.

The movements of the platform are measured by means of an acceleration sensor, wherein the distance covered is calculated from the measured value in order to quantify the measurement. Calculation errors are therefore also induced. Depending on the orientation of the test subject, either only a lateral or a frontal provocation is possible. Combinations with deflections in both horizontal axes cannot be carried out. The provocation unit must be mechanically released so as to start measurement. Although the device according to the prior art can be used for therapeutic purposes, the device is neither intended nor suited for use in diagnostics.

SUMMARY OF THE INVENTION

Therefore, the object of the invention is to overcome the disadvantages of the prior art. In particular, standardization of the measurement during posturography should be made possible. Furthermore, detection of the platform movement by means of position determination, synchronously with the acceleration measurements, should be made possible. A device with which parameters or measurement data can be determined, for diagnosis of coordination impairments, should be made available.

By way of the method and the device according to the invention, it is now possible to standardize the posturographic measurements by standardizing the zero position of the starting position for the measurement, to limit calculation errors, and to permit provocation in the lateral, frontal and diagonal directions as well as in any direction and any intensity with respect to the test subject. Mechanical or manual release of the provocation unit can be eliminated. Use of the device for determining measurement data and/or parameters for diagnostic purposes is made possible.

The invention will be described hereafter in the general form thereof.

By means of the device and the method according to the invention, the balance functions of a test subject can be analyzed. A test subject within the meaning of the invention can be a healthy person, a patient, or an animal.

The device according to the invention comprises a swingable platform on which the test subject can stand. The swingability can be given by means of a suspension on springs.

The platform interacts with an electromagnet, which is preferably attached under the platform and can be switched on and off by means of a power supply via a circuit. The electromagnet is displaceable in two axes, which preferably extend perpendicular to one another, parallel to the plane of the platform. As a result, the platform is deflectable. For this purpose, the electromagnet can be mounted on two rails, which are stacked perpendicular to one another and allow a movement of the electromagnet in two axes extending perpendicular to one another.

The electromagnet is connected to a power supply. The power supply can be, for example, a power pack or a battery.

In one special embodiment, the platform can be located in a frame or a rack in which the platform is suspended with springs.

Located under the frame is a plate (a), which is fixedly connected to the frame or the rack so that the position thereof is fixed.

Located on this plate (a) are rails, for example, on which a further plate (b) is located. The plate (b) is then movable on the plate (a) in two opposing directions.

Located on the plate (b) in this special embodiment is a further plate (c), which is movable on the plate (b) on rails in two opposing directions, which extend perpendicular to the directions in which the plate (b) can move. The electromagnet is located on the plate (c). By way of such an arrangement, which is shown here by way of example, the electromagnet can be brought into a desired position underneath the platform.

The platform comprises a magnetizable body, for example, a ferromagnetic metal body, for example, in the form of a metal plate, which reacts to the magnet. The magnetizable body or the metal plate made from ferromagnetic material can be affixed, for example, onto the platform. Preferably, the metal body is fastened under the platform.

The device can also comprise a computer, which controls the switching on and off of the electromagnet. This can take place via an analog/digital converter card (A/D converter card) and a circuit. The power supply can be connected to the A/D converter or to the circuit.

Within the meaning of the invention, an A/D converter is intended to mean a converter, which has an interface with an A/D converter and a D/A converter.

Signals should therefore be capable of being converted from analog to digital and from digital to analog.

In addition, the device can comprise lifting means, which make it possible to lift the electromagnet. By way of these lifting means, the electromagnet can be guided toward the magnetizable body or the magnetizable plate.

An acceleration sensor, which is connected to the computer via the A/D card, is attached on the platform.

The platform is preferably equipped with at least one position marker, which makes it possible to detect the exact position of the platform. Advantageously, multiple position markers, for example, two, three, or four position markers, are attached on the platform. Three, four, or more position markers have the advantage that a plane can be defined, whereby the measurement becomes more precise.

The device comprises a digital camera.

The digital camera captures the position of the position markers on the platform. On the basis of these positions, the movement of the platform is captured in the image sequences.

In addition, the device comprises a time-variable display, which is captured by the digital camera.

The time-variable display can be a holder on which lamps are attached, the lamps generating different patterns at different points in time, which can be registered by the digital camera. For example, multiple LED lamps can light up in different patterns and/or colors in predefined temporal sequences. The time-variable display can also be a clock or a temporally varying pattern, which can be displayed by means of display panels.

The time-variable display is connected to the computer via the A/D card.

Preferably, at least one additional position marker is associated with the time-variable display, the position marker being imaged with the digital camera, which makes it easier for the computer to recognize the position of the variable time display.

The digital camera can image the movement of the test subject.

The figure schematically illustrates the device according to the invention.

BRIEF DESCRIPTION OF THE DRAWING

FIG. 1: shows a schematic illustration of the device.

DESCRIPTION OF THE PREFERRED EMBODIMENTS

FIG. 1 shows a platform 1, which is equipped with an acceleration sensor 2 and on which a magnetizable body 3, in the form of a ferromagnetic metal plate, is attached. The acceleration sensor 2 is connected to an A/D converter 4. The A/D converter is connected to a computer 5. A position marker 6 is located on the platform 1. A time-variable display 7, which likewise has a position marker 8, is also connected to the A/D converter 4. The A/D converter 4 is connected to a circuit 9. The circuit 9 is connected to a power pack 10 and to an electromagnet 11. The electromagnet 11 is located on a plate 12, which is displaceable in two axes and is positioned on a further plate 13. In addition, the device comprises a digital camera 14, which is connected to the computer 5.

In the method according to the invention, the platform is initially fixed.

To this end, the electromagnet is supplied with current via the power supply and the circuit.

Preferably, the electromagnet is guided toward the electromagnetic body, which is located on the underside of the platform, by means of the lifting mechanism. As a result, a test subject standing upright on the platform is not exposed to great fluctuations. A defined zero position at the beginning of the measurement is therefore also ensured. Measurement can therefore be standardized.

The test subject positions itself on the fixed platform and assumes the desired posture.

When the measurement begins, the current is switched off, whereby the electromagnet is demagnetized.

If the current is switched off when the platform is in a rest position, provocation does not take place.

If a provocation is desired as the starting situation for the measuring process, the position of the electromagnet is changed before the switching-off, so that the platform moves into the desired starting position by means of the interaction between the magnetizable body and the electromagnet.

The electromagnet is switched off in the desired final position of the platform. An elongation with respect to the rest position is now present, proceeding from which the platform can swing. The switching on and off of the electromagnet can be controlled via the computer.

The test subject steps onto the platform (1) after the platform (1) has been fixed by means of the electromagnet (11).

Fixing of the platform by means of the electromagnet can take place in the zero position or in a deflected position.

Switching off the electromagnet in the deflected position results in a provocation. If the electromagnet is switched off when the platform is in the zero position, provocation does not take place.

Fixing the platform has the result that the starting position for the measurement is defined and the test subject proceeds from a rest position into a situation in which a provocation does not take place or, alternatively, in which a provocation is initiated. As a result, the method can be utilized for diagnostic purposes, because intra- and inter-individual comparability is ensured. For example, groups of persons of different ages or having different clinical profiles can be compared.

The measurement begins when the electromagnet is switched off.

The acceleration values are picked up by the acceleration sensor and are forwarded to the computer via the A/D card.

The digital camera captures the test subject, the platform with the position markers, as well as the time-variable display with the position markers associated therewith.

The image information of the digital camera is forwarded to the computer.

The measured acceleration data and the image information are stored.

Given that the acceleration and the position of the platform are measured independently of one another, calculation is not carried out. Possible calculation errors are therefore eliminated.

In a subsequent step, the computer associates simultaneous measurement data of the acceleration sensor and the digital camera with one another.

The computer preferably has pattern recognition software, which automatically recognizes the position markers or the platform in the images. The position markers, which can be recognized by the pattern recognition software, can be located on the platform, on the time-variable display, and/or on the test subject. In an alternative embodiment, the pattern recognition software can recognize the platform, the time-variable display, and/or the test subject without position markers.

The position of the platform is thereby detected.

The position of the time-variable display is recognized by the computer. By identifying the time-variable display, the computer can gather the time information, which is coded, for example, by means of lamps, LEDs, or another type of display, such as a clock, by means of suitable software. When lamps, such as LEDs, are used as the time-variable display, a multiplicity of lamps can be disposed next to one another, the lamps lighting up in a temporally varying pattern and making time assignment possible.

Preferably, the recognition of the time-variable display is simplified by means of the position markers associated therewith. To this end, the position markers are recognized by the computer. The position of the time display relative to the position marker is known and programmed. Therefore, the time information can be more easily identified.

As a result, the position data for the platform with the associated time information are available on the image data.

The data of the time-variable display, together with the data of the acceleration sensor, are forwarded via the A/D card to the computer and are stored. The time and acceleration data are therefore associated with one another.

The image information for a point in time and the acceleration data for the same point in time are therefore available.

In a further step, the image and the acceleration information for the same points in time are associated with one another.

Additionally, other signals can be measured, such as, for example, biological signals, for example, electromyogram and/or electrocardiogram and/or electroencephalogram.

In addition, non-biological signals, such as, for example, an audio signal, a signal from a clock generator, and/or a trigger signal can be measured by at least one other device.

For the case in which the sampling frequencies of the acceleration sensor and the digital camera are the same, the values must be associated 1:1.

For the case in which the sampling frequencies of the acceleration sensor and the digital camera differ, either the higher frequency would have to be subjected to a downsampling, or the lower frequency would have to be interpolated. Usually, a downsampling from higher to lower frequencies is carried out.

The movements of the test subject can likewise be imaged using the digital camera and forwarded to the computer. In this case, it is possible to attach markers at certain positions on the test subject, for example, at certain joint positions, the movement of which can be likewise imaged by the digital camera and forwarded to the computer. In addition, the test subject can assume a predefined posture with open or closed eyes.

The data obtained in this manner can be evaluated.

EXAMPLE

The invention is presented in the following by way of example but not in a limiting manner.

The system according to the prior art was enhanced with an electromagnet, an A/D converter, a Kinect camera, a webcam, and four position markers, whereby a standardized, computer-controlled measurement start is possible, and the acceleration of the platform can be detected by an acceleration sensor and the position thereof can be captured by a digital camera. The test subject and/or patient should perform exercises on the platform, which are typical for posturography (e.g., standing on both legs with open eyes and closed eyes or with the head tilted toward the back, standing on one leg, standing on both legs on a foam base with open eyes and closed eyes). In the developments, no irreversible structural changes were made to the main design of the platform, and therefore all parts are modular and can be removed again. The only change was to create holes (three on each corner, 12 holes in all) for additional screws in order to fix the electromagnet on the frame of the platform.

The electromagnet is mounted on a plate, which carries two rail systems, and can be deflected on two axes. This plate is located under the platform and is fastened thereto. The electromagnet is connected to the A/D converter, and therefore the activation/deactivation thereof can be controlled by means of a computer. Since the platform itself is not magnetic, a ferromagnetic plate (11.5 cm×10 cm×1 cm) was mounted (affixed) under the platform. The magnetization takes place by way of the power supply via a circuit. The synchronization of video images with the acceleration time series is carried out by means of a row of LEDs, which are sequentially activated/deactivated. The LEDs are located, together with their own position markers, on a separate holder, which is not fastened on the platform. These LEDs are automatically recognized in the video images. Since the LEDs additionally forward time stamps via the A/D converter card to the recording computer, synchronization of time series and video sequences is possible.

The invention claimed is:

1. A device for collecting data for posturography comprising:
   a swingable platform comprising a surface configured for a test subject to stand on and a magnetizable body;
   an acceleration sensor mounted on the swingable platform;
   an A/D converter which connects the magnetizable body and acceleration sensor to a computer;
   an electromagnet located under the platform and being movable relative to the platform, so as to be displaceable in two axes parallel to the plane of the platform, the electromagnet being connected to the A/D converter by a circuit, the electromagnet having a powered state during which current is received inducing a magnetic field, the magnetizable body reacting to the electromagnet;
   a time-variable display, which is connected to the A/D converter;
   a digital camera, the time-variable display and digital camera being connected to the computer; and
   a power supply that supplies said current to the electromagnet;
   wherein the swingable platform has a rest position toward which the swingable platform returns when power to the electromagnet is turned off;
   wherein the electromagnet has a first electromagnet location corresponding to said rest position for which no deflection of the swingable platform occurs while the electromagnet is in the first electromagnet location with the electromagnet receiving power from the power supply;
   wherein the electromagnet is configured to move away from said first electromagnet location to a second electromagnet location by being displaced in two orthogonal axes parallel to the plane of the swingable platform;
   wherein the swingable platform, including the magnetizable body, has a deflected position when the electromagnet is displaced relative to said first electromagnet location to said second electromagnet location while power to the electromagnet is on;
   wherein the deflected position of the swingable platform is based on magnetic interaction of the electromagnet and said magnetizable body while said electromagnet is displaced to said second electromagnet location and power to the electromagnet is on; and
   wherein said swingable platform, including said magnetizable body, is configured to return toward the rest position when the electromagnet is in the second electromagnet location and power to the electromagnet is turned off.

2. The device according to claim 1, wherein the the electromagnet is further configured to lift from underneath the swingable platform toward said magnetizable body.

3. The device according to claim 1, wherein the platform has at least one position marker.

4. The device according to claim 1, wherein the time-variable display has at least one position marker.

5. The device according to claim 4, wherein the time-variable display is a clock or a display having patterns varying in predefined time intervals.

6. The device according to claim 1, wherein the magnetizable body is a ferromagnetic metal body, which is attached at an underside relative to said surface.

7. The device according to claim 1, wherein the circuit for the electromagnet is connected to the computer via the A/D converter.

8. The device according to claim 1, further comprising a first assembly located under the platform and movable relative to the platform, the first assembly comprising a plate and the electromagnet located on the plate, and
  wherein the first assembly has a first location corresponding to said rest position for which no deflection of the swingable platform occurs while the first assembly is in the first location with the electromagnet receiving power from the power supply;
  wherein the first assembly is configured to move away from said first location to a second location by being displaced in two orthogonal axes parallel to the plane of the swingable platform;
  wherein the electromagnet is in the first electromagnet location while the first assembly is in the first location and is in the second electromagnet location while the first assembly is in the second location;
  wherein the swingable platform, including the magnetizable body, has a deflected position when the first assembly is displaced relative to said first position to said second position while power to the electromagnet is on.

9. The device according to claim 8, wherein said swingable platform, including said magnetizable body, is configured to return toward the rest position when the first assembly is in the second position and power to the electromagnet is turned off, said first assembly, including the electromagnet, remaining in said second position when power is turned off.

10. The device according to claim 8, further comprising a rail system to which the first assembly and swingable platform are mechanically coupled providing a path of movement of the first assembly along a first rail for a first axis of motion of the first assembly relative to said swingable platform and a second rail for a second axis of motion of the first assembly relative to the swingable platform, the first axis and second axis being orthogonal to one another and being parallel to a plane of the swingable platform.

11. A method for collecting data for posturography with a device comprising a swingable platform, including a surface configured for a test subject to stand on, a magnetizable body, and an an acceleration sensor mounted on the swingable platform, the device further including an A/D converter which connects the magnetizable body and acceleration sensor to a computer, an electromagnet located under the swingable platform movable relative to the swingable platform, the electromagnet being connected to the A/D converter by a circuit, the electromagnet having a powered state during which current is received inducing a magnetic field, a power supply supplying said current, a time-variable display which is connected to the A/D converter, and a digital camera, the time-variable display and digital camera being connected to the computer, the method comprising:
  supplying current to the electromagnet;
  moving the electromagnet away from a first electromagnet location to a second electromagnet location by displacing the electromagnet in two orthogonal axes that are parallel to a plane of the swingable platform, wherein the electromagnet is located at the first electromagnet location at a first time and is located at the second electromagnet location at a second time for each condition of a first condition in which power to the electromagnet is on and a second condition in which power to the electromagnet is off;
  deflecting the swingable platform from a rest position to a desired provocation position with said electromagnet by positioning the electromagnet in said second electromagnet location and magnetically interacting the electromagnet with said magnetizable body, the swingable platform being in said deflected position with said power to the electromagnet on; and
  with a test subject standing on the swingable platform, turning off power to the electromagnet, thereby releasing the magnetizable body from the magnetic interaction of the electromagnet so that the swingable platform returns toward said rest position, thereby inducing a provocation to the test subject, said swingable platform, including said magnetizable body, being configured to return toward the rest position when the electromagnet is in the second electromagnet location and power to the electromagnet is turned off;
  sensing as registered movement data registered movement of the swingable platform with the acceleration sensor;
  forwarding the sensed registered movement data via an A/D converter to the computer;
  forwarding time information data from the time-variable display to the computer via the A/D converter;
  capturing data with the digital camera, including a change of position of the swingable platform, movements of the test subject, and imagery of the time-variable display, wherein the captured data of the digital camera is forwarded to the computer; and
  correlating in time by said computer the sensed registered movement data of the acceleration sensor, the time information data of the time-variable display, and the captured data of the digital camera; and
  wherein said first electromagnet location of said electromagnet has a correspondence to said rest position of said swingable platform so that no deflection of the swingable platform occurs while the electromagnet receives power while the electromagnet is in said first electromagnet location.

12. The method according to claim 11, wherein the test subject assumes a predefined posture while standing on the swingable platform with open eyes or closed eyes.

13. The method according to claim 11, wherein the computer is configured to perform pattern recognition of position markers on the swingable platform.

14. The method according to claim 11, wherein the computer is configured to perform pattern recognition of a position marker on the time-variable display.

15. The method according to claim 11, in which the device further comprises a rail system to which the electromagnet and swingable platform are mechanically coupled providing a path of movement of the electromagnet; and in which the method step of moving comprises:
  moving the electromagnet away from the first electromagnet location to said second electromagnet location by displacing the electromagnet along the rail system, the rail system having a first rail for a first axis of motion of the electromagnet relative to the swingable platform and a second rail for a second axis of motion of the electromagnet relative to the swingable platform, the first axis and second axis being orthogonal to one another and being parallel to a plane of the swingable platform.

16. A method for collecting data for posturography with a device comprising a swingable platform, including a surface for a test subject to stand on, a magnetizable body, and an an acceleration sensor, the device further including an A/D converter which connects the magnetizable body and acceleration sensor to a computer, a first assembly located under the swingable platform movable relative to the swingable platform and including a plate and an electromagnet located on the plate, the electromagnet being connected to the A/D converter by a circuit, the electromagnet having a powered state during which current is received inducing a magnetic field, a power supply supplying said current, a time-variable display which is connected to the A/D converter, and a digital camera, the time-variable display and digital camera being connected to the computer, the method comprising:

supplying current to the electromagnet;

moving the first assembly away from a first position into a second position by displacing the first assembly in two orthogonal axes that are parallel to a plane of the swingable platform, wherein the electromagnet is located at a first electromagnet location while the first assembly is in the first location and is located at a second electromagnet location while the first assembly is in the second location for each condition of a first condition in which power to the electromagnet is on and a second condition in which power to the electromagnet is off;

deflecting the swingable platform from a rest position to a desired provocation position with said electromagnet by positioning the first assembly in said second position and magnetically interacting the electromagnet, located at the second electromagnet location, with said magnetizable body, the swingable platform being in said deflected position with said power to the electromagnet on; and with a test subject standing on the swingable platform, turning off power to the electromagnet, thereby releasing the magnetizable body from the magnetic interaction of the electromagnet so that the swingable platform returns toward said rest position, thereby inducing a provocation to the test subject, said swingable platform, including said magnetizable body, being configured to return toward the rest position when the first assembly is in the second position and power to the electromagnet is turned off;

sensing as registered movement data registered movement of the swingable platform with the acceleration sensor;

forwarding the sensed registered movement data via an A/D converter to the computer;

forwarding time information data from the time-variable display to the computer via the A/D converter;

capturing data with the digital camera, including a change of position of the swingable platform, movements of the test subject, and imagery of the time-variable display, wherein the captured data of the digital camera is forwarded to the computer; and correlating in time by said computer the sensed registered movement data of the acceleration sensor, the time information data of the time-variable display, and the captured data of the digital camera; and wherein said first position of said first assembly has a correspondence to said rest position of said swingable platform so that no deflection of the swingable platform occurs while the electromagnet receives power while the first assembly is in said first position.

17. The method according to claim 16, in which the device further comprises a rail system to which the first assembly and swingable platform are mechanically coupled providing a path of movement of the first assembly; and in which the method step of moving comprises:

moving the first assembly away from a first position into a second position by displacing the first assembly along the rail system, the rail system having a first rail for a first axis of motion of the first assembly relative to the swingable platform and a second rail for a second axis of motion of the first assembly relative to the swingable platform, the first axis and second axis being orthogonal to one another and being parallel to a plane of the swingable platform.

* * * * *